United States Patent [19]

Thompson

[11] 4,187,425
[45] Feb. 5, 1980

[54] PIPE INSPECTION SYSTEMS

[75] Inventor: Carroll R. Thompson, Odessa, Tex.

[73] Assignee: NDT Systems, Inc., Odessa, Tex.

[21] Appl. No.: 896,384

[22] Filed: Apr. 14, 1978

[51] Int. Cl.² ............................................. G01N 23/00
[52] U.S. Cl. ................................................. 250/358 P
[58] Field of Search ............... 250/358 P, 358 R, 359, 250/360

[56] References Cited

U.S. PATENT DOCUMENTS 3,683,186  8/1972  Tompkins ........................ 250/358 P
4,038,550  7/1977  Wassen et al. .................... 250/358 P Primary Examiner—Davis L. Willis

[57] ABSTRACT

The disclosed invention involves radioactive inspection of tubular pipe passed rotatively and longitudinally relative to an inspection head. A beam of radiation is directed so as to intersect the pipe along a chord where the intersection is spaced a distance "d" on a horizontal radius from the pipe axis, the distance "d" being approximately 0.6 of the radius of the outer pipe wall. A diametrical beam of radiation can be used for comparison purposes.

10 Claims, 7 Drawing Figures

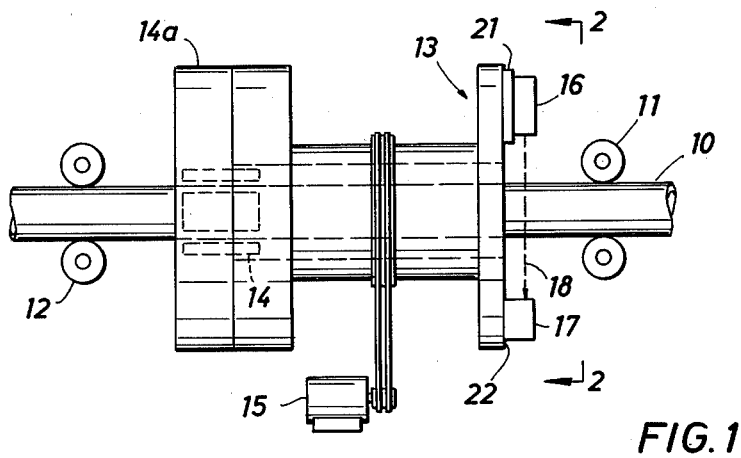
FIG.1
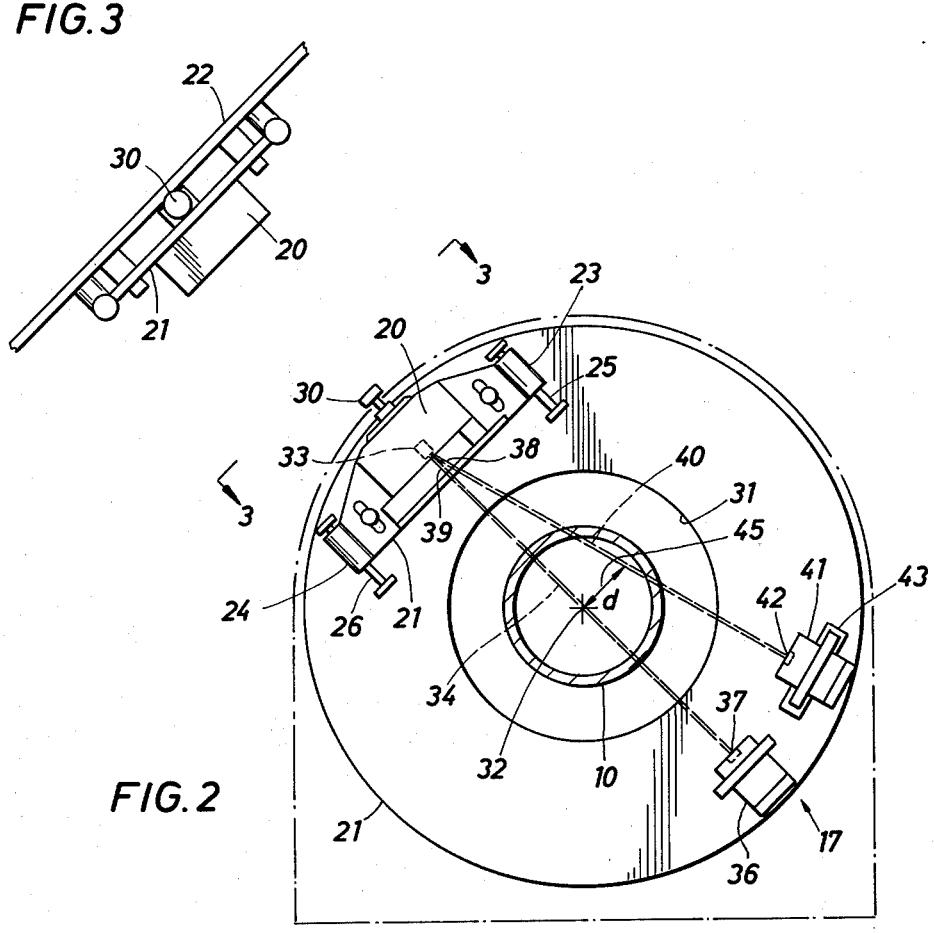
FIG.3
FIG.2

PIPE INSPECTION SYSTEMS

FIELD OF THE INVENTION

This invention relates to apparatus and methods for radioactive inspection techniques for evaluating the wall loss characteristics of a tubular wall of pipe member as well as the relative eccentricity of the inner and outer wall surfaces of the pipe member.

BACKGROUND OF THE INVENTION

Tubular pipe goods used in the oil field are typically inspected for hidden flaws and other defects in the pipe walls by electromagnetic and radioactivity inspecting techniques. With respect to radioactivity inspection techniques, one such technique involves measuring radioactivity which is back scattered from a pipe wall segment. In another radioactivity technique, radiation is passed diametrically through the pipe from a source to a detector and measures the cummulative wall thickness of wall segments at 180 degrees from one another. In still another radioactivity technique, the detector is located on a probe within the pipe so that radioactivity passes only through one wall segment.

In any of the foregoing inspection techniques, the tubular pipe is moved, longitudinally and rotatively, relative to the inspection device so that the inspection covers a helical section of the pipe. By adjusting the relative speeds, this inspection obtains adequate measurements.

One other factor of importance to inspection of pipe is its "eccentricity", i.e., the relative offset of the inner cylindrical wall surface to the outer cylindrical wall surface. Eccentricity occurs in pipe for a variety of reasons and becomes important when the pipe will be used in an oil or gas well. It is commonly accepted that a figure of 12.5% or less of eccentricity is acceptable. For example, with a 0.5 inch nominal wall thickness, the wall thickness is acceptable if it does not exceed plus or minus 0.0625 inches. Eccentricity is measured by the shift of the inner cylindrical surface relative to the outer cylindrical surface.

When a pipe is longitudinally and rotatively moved relative to an inspection head, tolerances of the equipment dictate that the pipe axis can be offset with respect to the axis of an inspection head. If the equipment tolerances cause an offset of the axes it is possible to have a situation where a concentrically perfect pipe produces a measurment similar to a measurment made for an eccentric pipe where the pipe and equipment axis are centered. In either instance, the measurement made through both sections of a pipe is actually a composite measurement including equipment offset affects and effects due to pipe eccentricity.

The present invention in one sense, involves a measurement through both walls of a pipe but is improved so as to eliminate source of weakness which is inherent in a system which passes diametrically through a pipe, this weakness being the inability to detect true eccentricity.

With respect to the apparatus for a typical radioactivity measuring system which diametrically measures through a pipe there is a radioactivity detector and a radioactive source diametrically located relative to one another on either side of a pipe. Typically, the source and detector are mounted on a vertical plate with a central opening so that as the plate is rotated about its axis, a pipe with its axis central with plate axis is longitudinally moved through the rotating plate. This system produces wall thickness measurements along a general helical path about the pipe. It would probably be ideal to move the pipe so slowly and rotate the radiation devices so fast that all of the pipe wall was inspected but as a practical matter this is not necessary and a helical path of inspection is an acceptable procedure.

SUMMARY OF THE INVENTION

The present invention involves use of a single radioactive source and collimating two beams of radioactivity from the source so as to pass diametrically through the pipe to be inspected and to pass angularly through the pipe respectively to each of two independent detectors. The source and detectors are mounted on a vertical face plate. The source and angular detector are arranged so that for different sizes of pipe their position can be changed so that an intersection of the beam of radioactivity with a horizontal axis through the pipe is located a distance "d" from the central axis of the pipe. The distance "d" is approximately equal to a factor of 0.6 times the radius for the outer cylindrical surface.

By field experience, the applicant has determined that if the ratio of the measurement signal for pipe having a 12.5 percent eccentricity to the measurement signal for a similar sized pipe having concentric walls but offset by equipment tolerances to equal 12.5 percent is greater than a 1.2 signal to noise ratio then eccentricity of pipe can be determined with a great deal of confidence by use of the present invention.

In another aspect of the present invention, a source and detector are offset and so that a beam of radiation is parallel to the diametrical axis and intersects a diametrical axis at a distance "d". In either embodiment the beam of radiation is along a chord of the pipe.

The novel features of the present invention are set forth in particular in the appended claims and the invention together with objects and advantages thereof will be best understood by way of the following description of the apparatus embodying the principals of the invention and illustrated in the accompanying drawings in which:

BRIEF DESCRIPTION OF THE DRAWINGS

FIG. 1 illustrates schematically a radioactivity measuring apparatus of the present invention as it may be arranged in connection with pipe to be inspected;

FIG. 2 is a view in cross-section taken along line 2—2 of FIG. 1;

FIG. 3 is a view in cross-section taken along line 3—3 of FIG. 2;

DESCRIPTION OF THE PREFERRED EMBODIMENT

Figure 4:
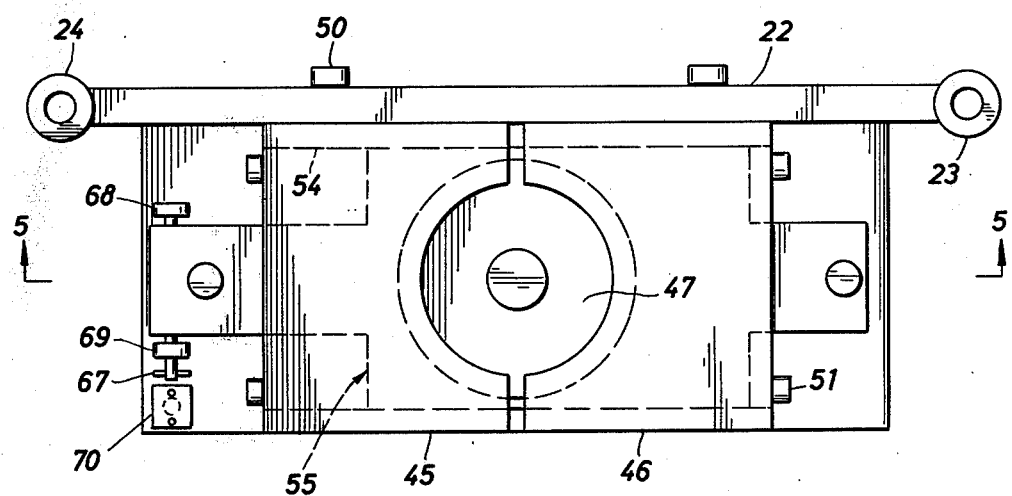
FIG. 4 is a detailed illustration of the source housing arrangement.

Referring now to FIG. 1, in the illustrated schematic plan view, a pipe or tubular member 10 is supported for movement along an axial direction by means of powered pinch rollers 11 and 12. Intermediate of the pinch rollers 11,12 is a spool-like rotating head 13 which is centered to rotate about axis of the pipe 10 being supported by the pinch rollers 11, 12. In addition, longitudinal shoes and coils 14 may be mounted on one end of the rotating head in a conventional manner for contact with the pipe 10 to provide electromagnetic field in the pipe for detecting lengthwise extending flaws. A flux extending ring 14a enhances the measurement. As will be appreciated, from the discussion to follow, the radioactivity detection system of the present invention is principally intended to detect wall thickness or loss and eccentricity.

At one side of the spool 13 is a driving motor 15 which can, for example, drive the rotating head 13 at a rotational speed of 60 to 80 revolutions per minute. The longitudinal speed of the pipe through the center of the spool 13 can be 40 to 60 feet per minute and is driven by rollers through the center of the spool 13. The relative speeds can be greater in some cases. The shoes 14 may be attached to the spool 13 so as to be rotated therewith or they can be separately mounted as may be desired. To one end of the rotating head or spool 13 is a source holder system 16 and a detector head system 17. The source holder 16 contains a radioactivity source such as 1500 millicuries of Cesium 137 which is collimated so as to pass vertically from the source holder system 16 to the detector head system 17.

As shown in FIG. 2, the source holder system 16 consists of a source housing 20 which mounted on a vertical support plate 21 which, in turn, is adjustably mounted with respect to a vertical back plate 22. The vertical backplate 22 is a part of the rotatable spool 13. The support plate 21 has parallel tubular cylindrically shaped parts 23, 24 which are slidably mounted on parallel shafts 25 and 26, respectively. The shafts are attached by brackets to the vertical back plate 22. Bolts through slotted holes in support plate 21 into vertical back plate 22 are used to lock the source housing 16 in place. To move the housing 20 relative to the back plate 22, a lead screw 30 is coupled between the back plate 22 and housing 20 so that upon rotation of the screw 30, the housing 20 is moved relative to the back plate 22.

The back plate 22 of the spool 13 has a central, cylindrical opening 31 about a central longitudinal axis 32. The spool 13 is rotatable about the axis 32 so that the housing 20 is rotatable about the axis 32. In the housing 20 is a radioactive source 33 which is collimated to project a beam of radiation 34 which intersects the central axis 32. The beam of radiation 34 and axis of the shafts 25, 26 are parallel to one another so that operation of the lead screw 30 adjusts the position of the source 33 toward and away from the axis 32. In direct alignment with the beam of radiation 34 is a scintillation counter 36 which has a window 37 to receive radiation. The beam of radiation 34 passing through the axis 32 passes diametrically through the pipe 10. The pipe 10 also has its longitudinal axis aligned with the axis 32. The housing 20 has an angularly arranged collimating aperature 38 which is at an angle of about 12 degrees relative to the diametrical aperature 39. The aperature 38 focuses a second beam of radiation 40 from the source 33 to a second scintilation counter 41 with a detecting window 42. The counter 41 is arranged on a slide mounting 43 to move in a direction transverse to the beam of radiation 40. The beam of radiation 40 intersects a perpendicular to the beam of radiation 34 where the perpendicular passes through the axis 32. The intersection of the beam of radiation 40 is at a distance "d" from the beam of radiation 34 along the perpendicular. The distance "d" by empirical determination should be approximately equal to 0.6 times the radius for the outer diameter of the pipe 10. It can thus be appreciated that if the distance "d" is determined for a size of pipe, the housing 20 and detector 41 can be positioned to align the beam of radiation 40 at the distance "d" from the axis 32.

Figure 5:
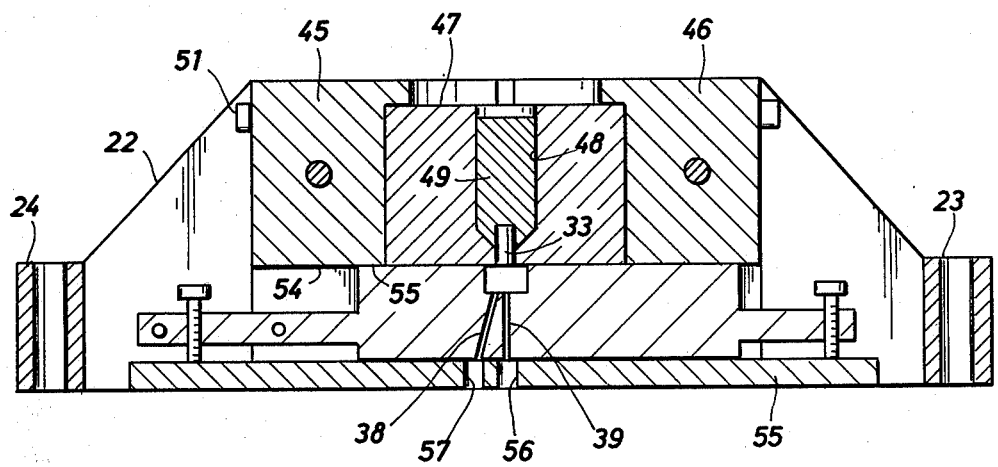
FIG. 5 is a view taken along line 5—5 of FIG. 4.

Referring now to FIG. 4, the base housing 20 consists of a pair of housing segments 45, 46 which enclose a cylindrically shaped source holder 47. The source holder 47 is constructed of heavy metal and has a central, vertical bore 48 which is arranged to receive a core insert 49 and a source capsule 33. The cylindrical source holder 47 provides a suitable radioactivity isolation for the source 33. The housings 45, 46 are bolted by bolts 50 to the plate 22 and by bolts 51 to one another. The housings 45, 46 are arranged so that there is a rectangular, elongated passageway 54 extending lengthwise of a base plate 55. Disposed in the rectangular passageway 54 is a rectangular shaped, elongated shutter block 55a which is also constructed of lead or heavy metal. The shutter block 55a is provided with a central vertical opening 39 which aligns with an aperture 56 in the base plate as well as an angular opening 38 or passageway which aligns with a second opening 57 in the base plate 55. Thus, in the position shown in FIG. 5 for the shutter block 55a, the source capsule 33 will project radiation through the passageways 38, 39 and the apertures 56, 57 both in a vertical direction and in an angular direction as directed by the openings in the shutter block.

At one end of the shutter block 55a is an elongated tang member 60 with a thumb screw 61 which provides a fastening for the shutter block in the open and closed positions. At the other end of the shutter block is a similar elongated tang member 62 which similarly has a thumb screw 63. The tang member 62 is provided with a pair of spaced openings 65, 66 through which a pin 67 can be inserted, the pin being also received in pin blocks 68, 69. The pin is also capable of being locked in place by a locking mechanism 70. As shown in FIG. 4, the locking mechanism 70 can be removable but when attached to the plate 55, the locking mechanism prevents the pin from being removed and thus locks the shutter block in position. When the lock 70 is removed, the pin can be removed, the thumb screws can be released, and the shutter block can be moved to a second position where the surface and thickness of the shutter block closes off the space between source capsule 33 and the base plate opening 70 so that no radiation may escape. In order to safely lock the shutter block in this closed position, the pin can be re-inserted through the opening in the tang member and through the pillow blocks and again locked in position. In short, the shutter block is slideable back and forth between open and closed positions relative to passing radioactivity from the source through the apertures 38, 39 to the detectors.

Figure 6:
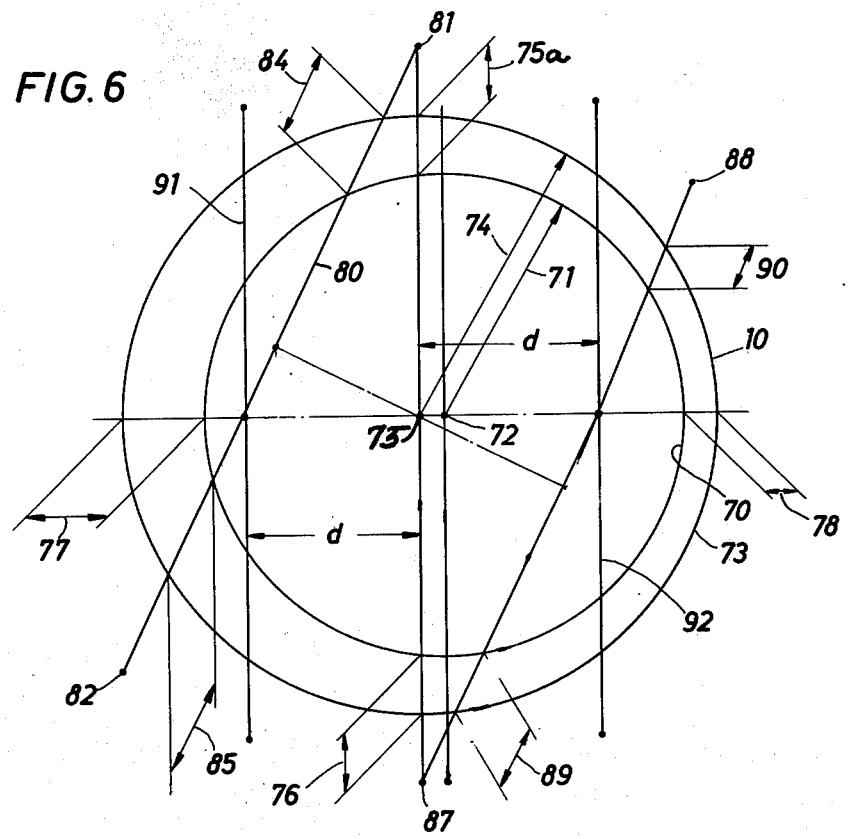
FIG. 6 is an illustration of an eccentric pipe for illustrative purposes.

Referring to FIG. 6, a pipe 10 shown in cross-section has an inner cylindrical wall 70 defined by a radius 71 from a center point 72 and an outer cylindrical wall 73 defined by a radius 74 from a axis 75. As illustrated graphically in the drawing, the sum of the wall thickness 75a and 76 along a vertical diametrical axis of wall 73 is equal to the sum of the wall thicknesses 77 and 78 along a horizontal axis of wall 73. Thus, if a source and detector are arranged to pass radioactivity diametrically through the pipe, the measurement will reflect the sum of the thickness of the opposing walls and this sum will be an equal amount over the full circumference of the pipe, irrespective of the wall thickness. On the other hand, a chord beam such as line 80 which passes from point 81 to a point 82 and intersects a transverse (or perpendicular) plane through the axis 75 at a distance "d" from the axis 75 passes through wall thicknesses 84 and 85. At a 180 degree position a similarly angled chord beam 86 passing from a point 87 to a point 88 and intersecting a transverse (or perpendicular) plane through the axis 75 at a distance "d" from the axis 75 at a distance "d" from the axis 75 passes through wall thicknesses 89, 90. The sum of wall thicknesses 84, 85 is greater than the sum of wall thicknesses 89, 90. Hence, a chord beam of radioactivity measures or produces a differing measurement which is indicative of the existence of eccentricity of the pipe.

As mentioned heretofore a diametrical beam is useful in determining wall loss. That is, if one wall segment is less than the other an indication of the loss is obtained. The chord measurement responds in the same fashion so that the chord measurement not only can indicate eccentricity but it can reflect wall loss as well.

Referring again to FIG. 6, vertical chords are illustrated at 91 and 92. The chords 91, 92 intersect the horizontal plane at the distance "d" and the difference in wall thickness summation for such chords are an indication of eccentricity.

The measurement of the "d" distance has been used because this is the optimum position located for obtaining reliable repetitive measurements and it will be appreciated that this measurement may be altered somewhat without losing the benefits of an eccentricity measurement.

Figure 7:
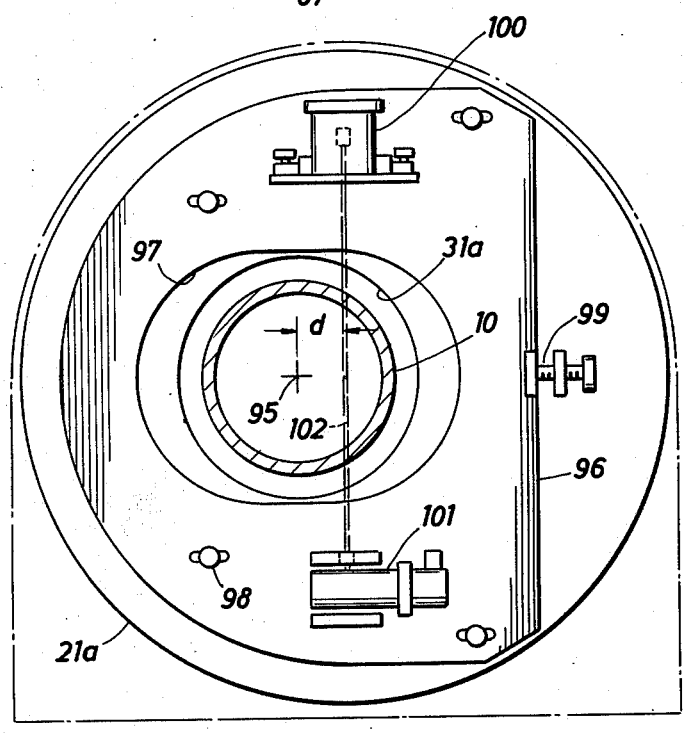
FIG. 7 is a view of another embodiment of the present invention.

Referring now to FIG. 7, a vertical back plate 21a has a cylindrical opening 31a for passage therethrough of a pipe 10. The pipe 10 has the central axis 95 for its outer cylindrical surface. Mounted on the back plate 21a is another plate 96 which has an elongated opening 97 and is attached to the back plate 21a by a plurality of bolts 98 which pass through elongated slots in the plate 96. As illustrated, the plate 96 can be shifted in a horizontal direction and this may be accomplished by means of a lead screw arrangement 99 attached between the back plate 21a and the plate 96. A source holder 100 is mounted on the upper part of the plate 97 and contains a source arranged to send a collimated beam of radioactivity 102 to a detector 101 which is mounted on the lower side of the plate 96. Thus, the source and detector are located on opposite sides of the pipe 10 and arranged to pass a beam of radiation 102 through a chord of the pipe. The beam of radiation 102 is arranged to be parallel to a diametrical axis, in this case a vertical diameter of the pipe 10, and by means of the thumb screw 99, the beam of radiation 102 can be located the distance "d" away from the axis 95. The beam of radiation can also be located so that it passes directly through the axis 95. Thus in this position the chord beam becomes a diametrical beam should the need arise. The adjustment 99 is provided for moving the beam of radiation 102 to accommodate different sized pipe so that the appropriate distance "d" may be obtained for the pipe size being inspected.

What is claimed is:

1. A method for radioactive inspection of a pipe member comprising the steps of:
    passing a beam of radiation through two wall segments of a pipe in a direction transverse to the axis of the pipe where the chord beam of radiation intersects a perpendicular radius for the outer wall of the pipe at a distance from the center axis which is a function of approximately 0.6 times the radius for the outer wall of the pipe;
    moving the pipe longitudinally and radially relative to the beam of radiation; and
    measuring the radioactivity transmitted through the wall segments as a function of angular and lengthwise positions of the pipe so as to provide a measure of pipe eccentricity.

2. The method as defined in claim 1 and further including the steps of:
    passing a second beam of radiation through two wall segments of a pipe in a direction through a diametrical axis of the pipe.

3. Apparatus for radioactive measurement of pipe comprising:
    an annular inspection head,
    means for moving said inspection head rotatively and longitudinally relative to an elongated pipe having a central axis;
    source means on said inspection head for generating a beam of radioactivity transverse to the axis of such pipe and intersecting a perpendicular radius at a distance located approximately 0.6 times the radius for the outer wall of a pipe to be inspected; and
    means on said inspection head for detecting such radioactivity wherein the detected radioactivity is a function of pipe eccentricity.

4. The apparatus as defined in claim 3 and further including in said inspection head, means for passing a beam of radioactivity diametrically through such pipe.

5. The apparatus as defined in claim 4 wherein said inspection head is rotated about its central axis, and further including means for moving a pipe along the central axis for said inspection head.

6. The apparatus as defined in claim 3 wherein said means for generating a beam of radioactivity and said detecting means are mounted on a plate means; and
    means movably mounting said plate means on said inspection head for adjusting the location of a beam of radioactivity relative to the axis of a pipe to be passed through the inspection head.

7. Apparatus for radioactive measurement of pipe comprising:
    an annular inspection head adapted for rotation about its central axis;
    means for moving said inspection head rotatively and longitudinally with respect to the longitudinal axis of an elongated pipe member where said longitudinal axis is aligned with said central axis;
    source means on said inspection head for generating a first beam of radioactivity in a direction transverse to and intersecting said central axis, and for generating a second beam of radioactivity in a direction and in a plane normal to said central axis, said second beam of radioactivity being at an angle to said first beam of radioactivity so as to intersect a radius perpendicular to said first beam of radiation at a distance "d" from said central axis;
    detector means on said inspection head for detecting said first and second beams of radioactivity; and
    means for adjusting the location of said source and detector means so that said distance "d" is equal to approximately 0.6 times the radius for an outer wall of a pipe to be inspected.

8. The apparatus as defined in claim 7 and further including in said source means, a source of radioactivity, a shielding housing surrounding said source of radioactivity, a shutter block having passages at an angle to one another for collimating radioactivity into two beams of radioactivity; and means for moving said passages in said shutter block into and out of operative relationship with respect to said source of radioactivity.

9. Apparatus for inspecting a tubular pipe for flaws comprising:

an annular inspection head;

means for moving said inspection head rotatively and longitudinally relative to an elongated pipe member having a central axis;

means on one end of said inspection head for contacting the pipe and for sensing longitudinal flaws in the pipe;

means on the other end of said inspection head for passing a beam of radioactivity transverse to the axis of such pipe and intersecting a perpendicular radius at a distance located approximately 0.6 times the radius for the outer wall of said pipe; and means on said inspection head for detecting such radioactivity wherein the detected radioactivity is a function of pipe eccentricity.

10. The apparatus as defined in claim 9 and further including means for rotating the inspection head about its central axis and means for longitudinally passing a pipe through said inspection head.

* * * * *